United States Patent [19]

Fancher

[11] 3,969,509
[45] July 13, 1976

[54] ORTHO-CARBAMYLOXY-BENZAMIDE BACTERICIDES

[75] Inventor: Llewellyn W. Fancher, Orinda, Calif.

[73] Assignee: Stauffer Chemical Company, Westport, Conn.

[22] Filed: Mar. 21, 1975

[21] Appl. No.: 560,841

Related U.S. Application Data

[62] Division of Ser. No. 466,107, May 2, 1974, Pat. No. 3,888,906.

[52] U.S. Cl. .................................................. 424/300
[51] Int. Cl.² ......................................... A01N 9/20
[58] Field of Search ................................... 424/300

[56] References Cited
UNITED STATES PATENTS

| | | | |
|---|---|---|---|
| 3,776,943 | 12/1973 | Peterson et al. | 260/471 C |
| 3,888,906 | 6/1975 | Fancher | 260/472 |

*Primary Examiner*—Leonard Schenkman
*Attorney, Agent, or Firm*—Michael J. Bradley

[57] ABSTRACT

This invention relates to the utility of certain benzamides as bactericidal agents having the formula

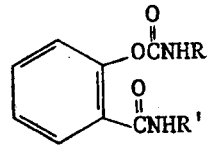

wherein R is halogen substituted phenyl, preferably mono or di halogen substituted at least one of which is in the meta position and R' is selected from the group consisting of hydrogen and phenyl. Said compounds are bactericidally active.

3 Claims, No Drawings

ORTHO-CARBAMYLOXY-BENZAMIDE BACTERICIDES

This is a division of application Ser. No. 466,107 filed May 2, 1974, now U.S. Pat. No. 3,888,906, issued June 10, 1975.

DETAILED DESCRIPTION OF THE INVENTION

This invention relates to the utility as bactercidal agents for the control of bacteria, when used in a bactericidally effective amount, of certain benzamides having the formula

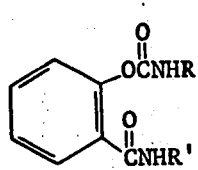

wherein R is halogen substituted phenyl, preferably mono or di halogen substituted at least one of which is in the meta position and R' is selected from the group consisting of hydrogen and phenyl. It has been found that these compounds have bactericidal activity and provide beneficial results in controlling the growth of bacteria.

Controlling the growth of bacteria by employing the compounds described herein can be accomplished by applying a bactericidally effective amount to the environment in which the growth of bacteria is encouraged. A specific example of such is the human mouth. Compounds may be applied to any environmental area which supports the growth and development of bacteria. By "controlling" is meant the prevention of the growth of the bacteria to be controlled.

The compounds of the present invention are prepared by the well-known reaction of an isocyanate with a compound having a reactive hydrogen such as found in alcohol, phenols, etc., as shown by the following equation:

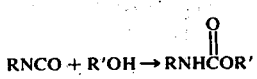

A wide variety of solvents and reaction conditions for conducting the above reaction are known to those skilled in the art.

The following examples demonstrate the preparation of compounds of the present invention.

EXAMPLE 1

2-N-3',4'-Dichlorophenyl carbamyloxybenzamide

Five and five-tenths grams (5.5 g) (0.04 M) of salicylamide was mixed with 25 ml. of dry acetone. To this mixture was added 3 drops of triethylamine (as a catalyst), followed by 7.5 g. (0.04 M) of 3,4-dichlorophenylisocyanate. The mixture was mixed and allowed to stand over night. The precipitated solid was filtered off and washed with acetone then washed with n-hexane and finally air dried. The product weighed 10.4 g. (80% of theory), m.p. 183°–184°C. The structure was confirmed by N.M.R.

EXAMPLE 2

2-N-3',4'-Dichlorophenyl carbamyloxybenzamides

By an identical procedure as was used in Example 1, 8.5 grams (0.04 M) of salicylanilide, 7.5 grams (0.04 M) of 3,4-dichlorophenylisocyanate, 3 drops of thiethylamine, 3 drops of dibutylindilaurate and 50 ml. of dry acetone gave, after reaction, 8.7 g. (54% of theory) of product, m.p. 164°–166°C. The structure was confirmed by N.M.R.

Other compounds of this invention are prepared in a similar manner.

The compounds examplified as bacteriologically active compounds are as follows:

COMPOUND I

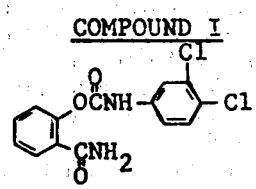

COMPOUND II

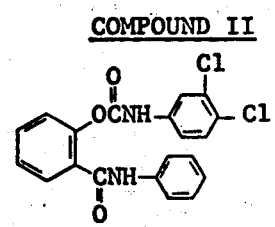

These compounds will hereinafter be referred to as Compound I and Compound II in the following examples.

EXAMPLE 3

Biocide Testing Procedure

Tubes of sterilized nutrient and malt extract broth are prepared. Aliquots of the toxicant, dissolved in an appropriate solvent, are injected through the stopper, into the broth, to provide concentrations ranging from 50 ppm downward. The test organism is a fungus, *Phoma herbarum*. Three drops of a spore suspension of the fungus are injected into the tubes of malt broth. One week later the growth of the organism is observed and effectiveness of the chemical is recorded as the lowest concentration in ppm which provides 50% inhibition of growth as compared to untreated inoculated tube. The results of these tests are tabulated in Table I.

TABLE I

|  | µgm/ml |
|---|---|
| Compound 1 | >50 |
| Compound 2 | >50 |
| >greater than | |

EXAMPLE 4

In Vitro Agar Screening Tests

This test measures the bactericidal, fungicidal and algaecidal properties of a compound when in contact with growing bacteria, fungi or algae in an artificial medium. The test is conducted by adding 20 ml. portions of a suitable warm sterile agar solution into 20 × 100 mm. Petri dishes. Then, the test compound, in 0.5% acetone solution, is added to the Petri dishes at levels of 1, 5, 10 and 50 μg/ml. and mixed with the warm mobile agar solution. The treated agar mixture is then allowed to come to room temperature and solidify. Cells of the chosen organism are streaked on the surface of the solidified agar and are then incubated for such lengths of time that untreated samples containing no toxicant show luxurious growth typical of the particular organism. This time varies from 24 hours to one week depending on the particular organism. The fungi are incubated at 30°C and the bacteria are incubated at 37°C. The algae are incubated at room temperature under artificial light. Nutrient agar is used as the medium in this test for the bacteria. Potato dextrose agar is used as the medium for the fungi with the exception of Trichophyton mentagroyphytes for which Emmons agar is used. A modified Jack Meyers agar is used for the growth of the algae.

The extent of growth is noted at the end of the incubation period.

Representative organisms used in this test are as follows:

Bacteria
- Bacillus cereus
- Brevibacterium ammoniagenes
- Enterobacter aerogenes
- Escherichia coli
- Pseudomonas aeruginosa
- Pseudomonas fluorescens
- Sphaerotilus natans

Fungi
- Asperigillus flavus
- Aspergillus fumigatus
- Aspergillus niger
- Aspergillus oryzae
- Aureobasidium pullulans
- Pencillium expansum
- Pencillium italicum
- Pencillium ochra-chloron
- Pencillium vermiculatum
- Rhizopus stolonifer
- Trichoderma sp.
- Trichophyton mentagrophytes

Algae
- Chlorella pyrenoidosa
- Euglena gracilis
- Scenedesmus obliquus

TABLE II

In Vitro Agar Screening Tests
Minimum Inhibitory Concentration, μg/ml.

| | Compound Number | |
|---|---|---|
| | I | II |
| Bacteria | | |
| Bacillus cereus | (5) | 1 |
| Brevibacterium ammoniagenes | 5 | 5 |
| Enterobacter aerogenes | >50 | (50) |
| Escherichia Coli | 50 | >50 |
| Pseudomonas aeruginosa | >50 | >50 |
| Pseudomonas fluorescens | >50 | >50 |
| Sphaerotilus natans | 50 | |
| Fungi | | |
| Asperigillus flavus | >50 | >50 |
| Aspergillus fumigatus | >50 | >50 |
| Aspergillus niger | >50 | >50 |
| Aspergillus oryzae | >50 | >50 |
| Aureobasidium pullulans | >50 | >50 |
| Pencillium expansum | >50 | 50 |
| Pencillium italicum | >50 | >50 |
| Pencillium ochra-chloron | >50 | >50 |
| Pencillium vermiculatum | | |
| Rhizopus stolonifer | >50 | >50 |
| Trichoderma sp. | >50 | 50 |
| Trichophyton mentagrophytes | (50) | (50) |
| Algae | | |
| Chlorella pyrenoidosa | 50 | 10 |
| Euglena gracilis | >50 | >50 |
| Scenedesmus obliquus | >50 | 50 |

( ) indicates partial control at this concentration
> indicates greater than

EXAMPLE 5

Sulfate Reducing Bacteria in Vitro Test

This test measures the bactericidal properties of a compound when in contact with a sulfate reducing bacteria, specifically Desulfovibrio desulfuricans. The test is conducted by dissolving the test compound in acetone to give an 0.5% solution. This toxicant is added to vials containing sterile Sulfate API broth with tryptone under anaerobic conditions at such levels to give final toxicant concentrations of 1, 5, 10 and 50 μg/ml. of solution. An inoculant solution of 0.5 ml. of the growing organism, Desulfovibrio desulfuricans, is added to the vials followed by sufficient sterile distilled water to give a total of 10 ml. solution in the vials. The vials are incubated at room temperature for 3 to 5 days until untreated controls show growth of the organism as indicated by the black color development in the vials.

The following is a summary of the minimum inhibitory concentration necessary to control the organism.

TABLE III

| | μg/ml. | |
|---|---|---|
| | Compound I | Compound II |
| Desulfovibrio desulfuricans | (50) | 50 |

( ) indicates partial control at this concentration.

EXAMPLE 6

Staphylococcus Aureus Use Dilution Test

This test measures the bacteriostatic effectiveness of a particular test compound against Staphylococcus aureus.

Tryptic Soy Broth is despensed aseptically into sterile 13 × 100 mm. clear glass culture tubes. The first tube receives 3.6 ml. of medium and tubes 2 through 10 receive 2.0 ml. of medium. The test compound is dissolved in acetone to give 10 ml. of a solution of 0.10% of the test compound. Using a sterile syringe, 0.4 ml. of the test compound solution is placed in the first tube containing the 3.6 ml. of sterile broth and mixed thoroughly. This operation is continued through to the tenth tube. From the tenth tube, 2.0 ml. of solution is removed and discarded. Each tube is then innoculated with 0.1 ml. of a 24 hour culture of Staphylococcus aureus in Tryptic Soy Broth, and the mixture is mixed thoroughly using a Vortex mixer. A control is also set up to be sure that the inoculum is viable using a tube of sterile broth containing no added toxicant. The tubes are incubated for 24 hours at 37°C. The tubes are then examined to determine growth of the organism in the culture tubes. The minimum concentration in which no growth of the organism occurs is recorded. The following table gives the minimum inhibitory concentration necessary to control the organism.

TABLE IV

| Toxicant | Minimum Inhibitory Concentration. Staphylococcus aureus, μg/ml. |
|---|---|
| Compound I | 0.39 |
| Compound II | 6.25 |

BIOCIDE TESTING PROCEDURES

Tubes of sterilized nutrient and malt extract broth are prepared. Aliquots of the toxicant, dissolved in an appropriate solvent, are injected through the stopper, into the broth to provide concentrations ranging from 50 ppm downward. The test organisms consist of two fungi, *Aspergillus niger* van Tieghem and *Penicillium italicum* Wehmer, and two bacteria, *Escherichia coli* Migula and *Staphylococcus aureus* Rosenbach. Three drops of a spore suspension of each of the fungi are injected into the tubes of malt broth and three drops of the bacteria are injected into the nutrient broth. One week later the growth of each organism is observed and effectiveness of the chemical is recorded as the lowest concentration in ppm which provides 50% inhibition of growth as compared to untreated inoculated tubes.

TABLE V

| Compound Number | Aspergillus Niger | Penicillium Italicum | Escherichia Coli | Staphlococcus Aureus |
|---|---|---|---|---|
| I | >50 | >50 | >50 | .03 |
| II | 25 | 1 25 | >50 | .016 |

The compounds of this invention are generally embodied into a form suitable for convenient application. For example, the compounds can be embodied into pesticidal compositions which are provided in the form of emulsions, suspensions, solution, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents such as sesame oil, xylene range solvents, heavy petroleum, etc; water; emulsifying agents; surface active agents; talc; pyrophyllite; diatomite; gypsum; clays; propellants, such as dichlorodifluoromethane, etc. If desired, however, the active compounds can be applied directly to feedstuffs, seeds, etc. upon which pests feed. When applied in such a manner, it will be advantageous to use a compound which is not volatile. In connection with the activity of the presently disclosed pesticidal compounds, it should be fully understood that is is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present pesticidal compositions can vary within rather wide limits, ordinarily the pesticide compound will comprise not more than about 15.0% by weight of the pesticidal composition. Preferably, however, the pesticidal compositions of this invention will be in the form of solutions or suspensions containing about 0.1 to 1.0% by weight of the active pesticide compound.

What is claimed is:

1. A method of controlling bacteria comprising applying to the habitat thereof a bactericidally effective amount of a compound having the formula

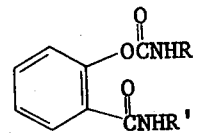

wherein R is halogen substituted phenyl at least one of said halogen substituents being in the meta position and R' is selected from the group consisting of hydrogen and phenyl.

2. The method of controlling bacteria as set forth in claim 1 wherein R is

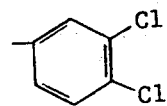

and R' is H.

3. The method of controlling bacteria as set forth in claim 1 wherein R is

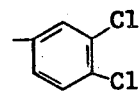

and R' is phenyl.

* * * * *